US00PP13261P2

(12) United States Plant Patent
Kent

(10) Patent No.: US PP13,261 P2
(45) Date of Patent: Nov. 19, 2002

(54) GUZMANIA PLANT NAMED 'GUZ 229'

(75) Inventor: Jeffrey C. Kent, Encinitas, CA (US)

(73) Assignee: Kent's Bromeliad Nursery, Inc., Vista, CA (US)

( * ) Notice: Subject to any disclaimer, the term of this patent is extended or adjusted under 35 U.S.C. 154(b) by 51 days.

(21) Appl. No.: 09/761,928

(22) Filed: Jan. 17, 2001

(51) Int. Cl.[7] ..... A01H 5/00

(52) U.S. Cl. ..... Plt./371

(58) Field of Search ..... Plt./371

*Primary Examiner*—Kent L. Bell
(74) *Attorney, Agent, or Firm*—James A. Lucas; Driggs, Lucas, Brubaker & Hogg Co., L.P.A.

(57) ABSTRACT

A compact Bromeliad hybrid having large dark red floral bract coloration and medium foliage. The size of the plant and the foliage makes this hybrid suitable for growing in 4"–5" containers.

1 Drawing Sheet

BOTANICAL CLASSIFICATION

*Guzmania lingulata×squarossa.*

VARIETY DENOMINATION

'GUZ 229'.

BACKGROUND OF THE INVENTION

The present invention relates to a newly developed interspecific hybrid Guzmania plant *Guzmania lingulata× squarossa* resulting from a planned breeding program that I conduct on an ongoing basis. The objects of the breeding program include the crossing of selected parent plants from the numerous, compatible species within the genus, to obtain plants with novel and attractive phenotypes, coloration, and flowering forms. Other important selection factors may include ultimate plant size and shape, disease resistance, tolerance to different soil and growing conditions and vigor.

Among the objects of my program are to produce plants of the Bromeliaceae family which will be attractive to the consumer; which will develop reasonably rapidly under controlled conditions, and which retain for a long term, highly attractive and bright inflorescence; i.e., bract coloration, after being induced into the flowering stage. It is a specific object to provide a low maintanance plant which will be a long term decorative appointment offering an exotic color splash in the home of a buyer, or to serve as a substitute for flowering plants which have a shorter flowering duration in, for example, indoor plant and flower scapes. Finally, it is an object to develop plants which may be easily and efficiently multiplied by state-of-the-art tissue culture methods while continuing the distinctive characteristics of the plants through progressive clonal generations.

The plant of this disclosure was a selection from the progeny resulting from the cross of a seed parent *Guzmania lingulata* 'Panama' (unpatented) with a pollen parent *Guzmania squarossa* 'Pink' (unpatented). With the recognition that this seedling from the cross satisfied the objects of the breeding program, the individual was isolated and set aside for further observation and testing. The resulting selection has been assigned the designation 'GUZ 229' for purposes of identification. This plant has been reproduced by tissue culture under controlled conditions at Evergem Belgium, and the clonal specimens resulting therefrom have been determined to be identical to the original selection in all distinguishing characteristics.

This plant is compared with its parents in the following respects:

*Guzmania lingulata* 'Panama' is 9" tall and 17" wide. Its foliage color is 143A adaxial and 144B abaxial. Leaf length is 9–10" and width is 1" to 1¼". Inflorescence is 6"–7" tall and 4¾" to 5½" wide. Floral and scape bracts adaxial 43B, abaxial 40A.

*Guzmania squarossa* 'Pink' is 18"–20" tall by 12"–26" wide. Leaf length is 13"–15" long by 1½"–1¾" wide. Foliage color is 146B adaxial and 144C abaxial. Base of scape and floral bracts are 146B adaxial and 144C abaxial, staining through the middle of scape bract 63A back to 146B adaxial and 144C abaxial at tips. Upper floral bract remain 63A at tips.

The superior attributes of this plant will be revealed in the botanical descriptions to follow.

SUMMARY OF THE INVENTION

The attributes of the plant 'GUZ 229' which distinguish it from the other similar Guzmania hybrids known to me are described as follows:

The hybrid shows unique dark red floral bract coloration, large sized flowers and medium-sized foliage. The plant size and inflorescence size makes the hybrid ideal for growth in 4" and 5" containers. 'Guz 229' is relatively fast growing, reaching marketability in less than two years from a 1" plant. The bracts retain good color for 12 to 14 weeks under interior light conditions.

BRIEF DESCRIPTION OF THE DRAWING

The single color photograph depicts a mature plant in mid to late flowering stage. Illustrated are the mature leaves, scape bract and primary bract. The color definitions in the specification have been taken from The R.H.S. Colour Chart of The Royal Horticultural Society. The colors depicted are believed to be of a high level of color fidelity and are believed to be as close to the actual coloration of the plant as possible in a photographic illustration of this quality. However, due to factors such as light reflectance, cultural conditions and horticultural practices, the coloration of this plant should be understood to be approximate. For example, the bract color might slightly fade if the plant is subjected to bright light and the leaf color may vary depending on the composition and the concentration of fertilizer which may be applied to the plant.

BOTANICAL DESCRIPTION OF THE PLANT

Age of observed plant: 46 weeks.
Parentage:
*Seed parent.*—*Guzmania lingulata* 'Panama'.
*Pollen parent.*—*Guzmania squarossa* 'Pink'.
Propagation:
*Method of asexual reproduction.*—Tissue culture.
*Where reproduction took place.*—Evergem, Belgium.
Plant: Type-monocot perennial.
*General characteristics.*—Medium in size: Overall height from soil surface including inflorescence—12.5". Overall spread—16".
*Habit.*—Vase formed, compact. Not tolerant to temperatures below 43° F.
Leaves:
*Quantity.*—Normal for the species.
*Medium in size.*—Length 10–13". Width: ¾" to 1¼" (mid length).
*Shape.*—Lanceolate; tip acute.
*Attitude.*—Ascending.
*Texture.*—Smooth upper and under sides.
*Margin.*—Smooth.
*Stipules.*—None.
*Ribs and veins.*—Not visually prominent.
*Coloration.*—New and mature foliage — RHS 146B adaxial and 146C abaxial.
Inflorescence: A branched spike.
Scape bracts:
*Lower.*—Size 12" by 1½". Shape: lanceolate, tip acute. Margin — entire. Color: 53B at base staining into 146B towards tip (adaxial and abaxial).
*Upper.*—Size: 5"×1¼". Shape: Lanceolate, tip acute. Margin — entire. Attitude — ascending. Texture — smooth upper and lower sides. Ribs and veins — not visually prominent. Color: 53B adaxial and abaxial.
Primary bracts:
*Size.*—4"×1".
*Shape.*—Lanceolate, tip acute.
*Margin.*—Entire.
*Attitude.*—Ascending.
*Texture.*—Smooth upper and lower sides.
*Ribs and veins.*—Not visually prominent.
*Color.*—RHS 53B abaxial and adaxial.
Floral bracts:
*Size.*—3.5" to 1¾" in length; 1" to ¾" in width.
*Shape.*—Lanceolate, tip acuminate.
*Margin.*—Entire.
*Attitude.*—Ascending.
*Texture.*—Smooth upper and lower sides.
*Ribs and veins.*—Not visually prominent.
*Color.*—53B, 53A at apex (adaxial and abaxial).
Bud:
*Size.*—Medium, 1" by ½'.
*Form.*—Ovoid.
*Color.*—When sepals first divide: 61B (adaxial and abaxial). When petals begin to unfurl: 9C (adaxial and abaxial). At anthesis: 6B adaxial surface of petals and 7A abaxial surface of petals.
*Sepals.*—Shape — Lanceolate with pointed tip. Margin — Entire. Number — 3. Size — ⅞"×3/16". Color — 151D, translucent (adaxial and abaxial). Loses color at tip which is very translucent.
*Calyx.*—Shape — funnel. Size — small, ¼"–⅜". Aspect — smooth. Odor when rubbed — none.
*Peduncle.*—Nested in floral scape bract.

FLOWER

Blooming habit:
*Location where observations were made.*—Coastal southern California.
*Time of year.*—April.
*Time of day.*—Approximately noontime. Blooms once.
*Other habit.*—In mature plant, full color is reached in 14 weeks after induction at any time of year.

INFLORESCENCE

Average size when fully expanded: 6.7" to 7" wide, 7" to 8" tall.
Borne: Singly.
Form: When first open: tubular; retains its form until flower desiccates.
Petalage: Number of petals under normal conditions: 3 in a single row fused at base.
Color:
*Center of flower* (*adaxial*).—6B.
*Petals* (*adaxial*).—6B from fused base to tip.
*Petals* (*abaxial*).—3D at fused base, 7A, 9C at tip.

PETALS

Texture: Soft. Unaffected by wet or hot weather.
Appearance: Abaxial and adaxial: shiny. Form: Oval.
Arrangement: Imbricate. No petaloids in center.
Persistence: Hang on and dry.
Fragrance: None.
Lastingness: 3 days.
As cut flower: Fair — 7–14 day.

REPRODUCTIVE ORGANS

Stamens:
*Anthers.*—Size: Medium — ⅛" long. Number: 5 . Color — 1C. Arrangement — Regular around styles.
*Filaments.*—Threads: Short — ¼". Color — 2D.
Pollen: Color — 1D.
Pistil: 1 per flower.
*Length.*—13/16".
*Color.*—2D.
*Styles.*—Loosely separated. Length — Short — 11/16".
*Stigmas.*—Color 2D.
*Ovaries.*—Superior; enclosed in calyx.
Fruit: A three celled capsule splitting longitudinally when mature, seeds with pappus-seeds not viable.
Susceptibility to disease and pests: None observed to date.

What is claimed is:

1. A new and distinct variety of Guzmania plant named 'Guz 229' as illustrated and described herein.

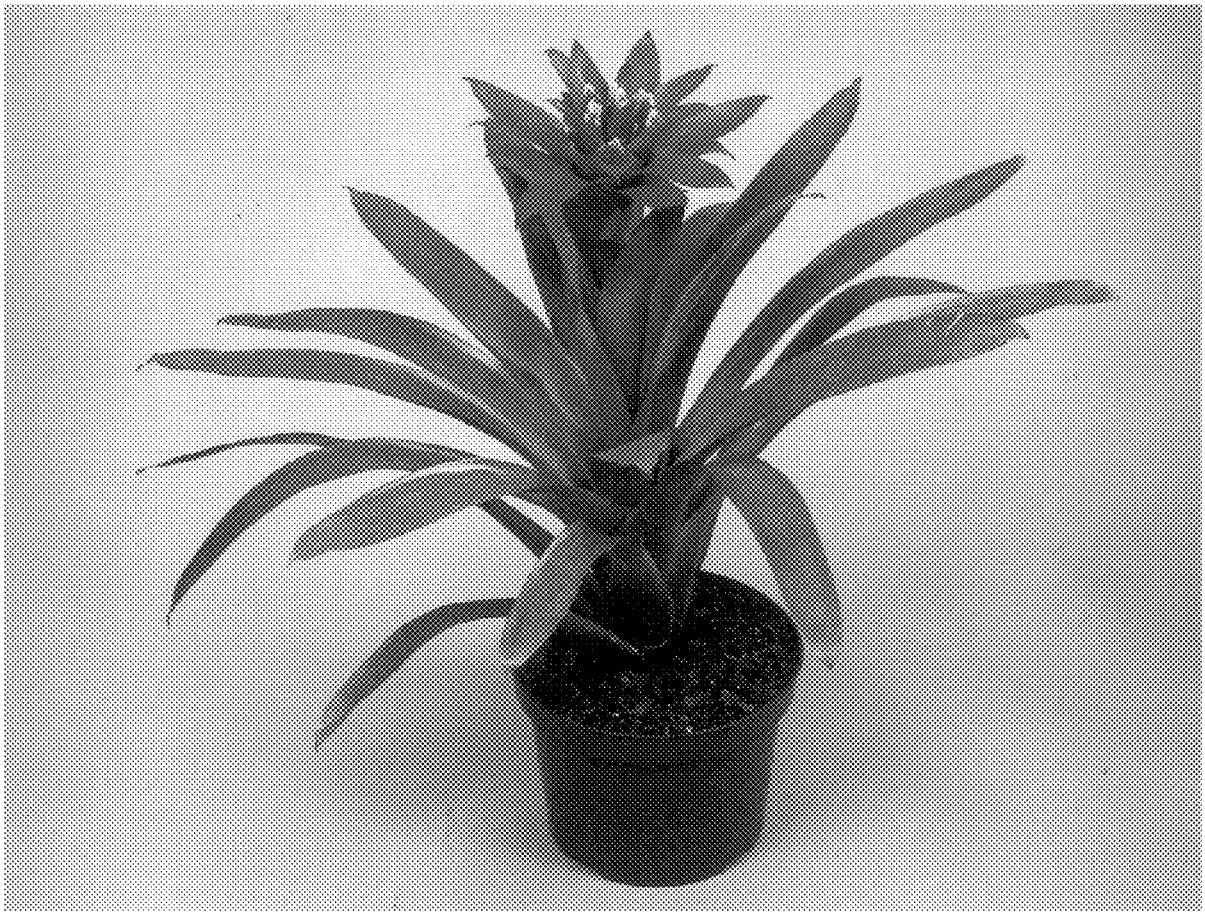

* * * * *